United States Patent [19]

Villa et al.

[11] 4,290,817

[45] Sep. 22, 1981

[54] GLUCOHEPTONATE COMPOSITION

[75] Inventors: José L. Villa, Bridgewater; Joseph V. Sinka, Mendham; Joseph P. Fleming, East Brunswick, all of N.J.

[73] Assignee: Diamond Shamrock Corporation, Dallas, Tex.

[21] Appl. No.: 112,564

[22] Filed: Jan. 16, 1980

[51] Int. Cl.$^3$ .................................................. C04B 7/02
[52] U.S. Cl. ....................................... 106/315; 106/90
[58] Field of Search ................................... 106/90, 315

[56] References Cited

U.S. PATENT DOCUMENTS

| | | | |
|---|---|---|---|
| 3,100,526 | 8/1963 | Martin | 106/315 |
| 4,028,125 | 6/1977 | Martin | 106/90 |
| 4,137,088 | 1/1979 | Debus et al. | 106/90 |

FOREIGN PATENT DOCUMENTS 7802246  8/1979  France ................................ 106/315

*Primary Examiner*—James Poer
*Attorney, Agent, or Firm*—Leslie G. Nunn, Jr.

[57] ABSTRACT

Byproduct ammonium ions remaining in an aqueous solution of a water soluble glucoheptonate salt after its synthesis are reacted with the free acid form of a naphthalenesulfonic acid-formaldehyde condensation product to obtain an aqueous composition which does not produce an ammonia odor when introduced into aqueous media having a pH above 9. The aqueous composition can be dried to obtain a flowable powder. Both the aqueous composition and flowable powder are useful as additives in industrial products. They may be used to prolong the time of hydration of cement.

6 Claims, No Drawings

GLUCOHEPTONATE COMPOSITION

BACKGROUND OF THE INVENTION

1. Field of the Invention

This invention relates to glucoheptonate compositions and their use in industrial products.

2. Description of the Prior Art

Glucoheptonates such as sodium glucoheptonate were not commercially available until 1962 because suitable processes for their manufacture had not been developed.

U.S. Pat. No. 3,022,343—Behnke, issued Feb. 20, 1962, describes a process for producing sodium glucoheptonate syrup from commercial corn syrup and sodium cyanide. Solid sodium cyanide was added rapidly as a single charge to an aqueous solution of corn syrup having an initial temperature of 0° to 30° C. Sodium cyanide stoichiometrically equivalent to the combined dextrose and maltose content of the syrup, calculated as glucose was added. The reaction mixture was agitated until all of the cyanide was in solution and reaction was complete. Upon completion of reaction, the reaction mixture was simultaneously aerated and heated gradually to 70° C. The reaction mixture was aerated and maintained at 70° C. until no trace of cyanide was present in the mixture.

U.S. Pat. No. 2,141,569—Tucker et al, issued Dec. 27, 1938, describes preparation and use of an alkali salt of a condensation product of naphthalenesulfonic acid and formaldehyde as a dispersing agent for cement particles to increase plasticity of a cement concrete mix.

U.S. Pat. No. 4,137,088—Debus et al, issued Jan. 30, 1979, describes an additive combination for water containing setting building materials such as those based on cement containing an anionic polyelectrolyte, a low foaming nonionic surfactant and optionally a polyhydroxy monocarboxylic acid or polyhydroxy dicarboxylic acid. An additive combination of a salt of an anionic higher molecular weight condensation product of sulfonated naphthalene/formaldehyde resin, a block polymer of 90% of propylene oxide and 10% of ethylene oxide and a glucoheptonate salt is proposed.

Sodium glucoheptonate is also useful as a chelating agent in compositions for cleaning glassware and metals, paint stripping compositions, boiler scale removing compositions, radiator cleaners, germicidal compositions and the like. Sodium glucoheptonate is usually sold commercially in solution because it becomes a tacky substance on drying. It also has an ammoniacal odor resulting from byproduct ammonia which is objectionable to personnel handling glucoheptonate on an industrial scale.

Sodium salts of naphthalenesulfonic acid-formaldehyde condensates such as Lomar® D are used commercially as dispersing agents for cement particles in cement and concrete mixes.

SUMMARY OF THE INVENTION

Byproduct ammonium ions remaining in an aqueous solution of a water soluble glucoheptonate salt after its synthesis are reacted with the free acid form of a naphthalenesulfonic acid-formaldehyde condensation product to obtain an aqueous composition which does not produce an ammonia odor when introduced into aqueous media having a pH above 9. From about 2 to about 50% by weight of naphthalenesulfonic acid-formaldehyde condensation product is added to 50% by weight solution of water soluble salt such as sodium glucoheptonate. The resulting aqueous composition can be dried to obtain a flowable powder. Both the aqueous composition and flowable powder are useful as additives in industrial products such as hydraulic cement mixes. From about 0.05 to about 3% by weight (dry basis) of sodium glucoheptonate aqueous composition or powder based on weight of cement may be added to a cement mix to prolong the time of hydration of cement.

DESCRIPTION OF THE PREFERRED EMBODIMENTS

Water soluble glucoheptonates such as sodium, potassium, lithium, calcium, magnesium or zinc glucoheptonate may be used in these compositions.

Sodium glucoheptonate is prepared by adding to an aqueous solution of corn syrup cooled to a temperature in the range of 0°–30° C., preferably 0°–20° C., a quantity of sodium cyanide stoichiometrically equivalent to the dextrose and disaccharide content of the syrup, calculated as the glucose equivalent and agitating the reaction mixture until the sodium cyanide is completely dissolved. When this procedure is followed, aldoses and disaccharides present in corn syrup react with sodium cyanide before these sugars can be degraded by alkali liberated by hydrolysis of sodium cyanide.

Within 3 to 4 hours after sodium cyanide addition, the reaction mixture is simultaneously aerated and heated to a temperature not in excess of 70° C. and maintained at that temperature under these conditions until no trace of cyanide is present in the mixture. Any suitable test for cyanide may be used. The Pagenstecher-Schonbein test is an excellent cyanide test.

After removal of cyanide, solids content of the sodium glucoheptonate syrup may be adjusted and cooled to room temperature. If necessary, the syrup may be concentrated by vacuum evaporation to 50% solids. Syrup produced by this procedure is light amber in color and has a high sequestering capacity for metal ions such as calcium, magnesium, iron, zinc and the like. Alkalinity of the syrup is in the pH range of 10–7.5.

Commercially available corn syrups are essentially mixtures of dextrose, maltose, higher sugars and dextrins. Proportions of these components vary depending on methods employed in manufacturing the corn syrup. Dextrose and maltose are the major components in the syrup. Dextrose is an aldose and maltose is a disaccharide. The term "higher sugars" includes those sugars not falling within the collective group of aldoses and disaccharides. The term "sodium glucoheptonate syrup" includes not only the sodium glucoheptonates formed in the reactions involved in the above process but also the sodium salts of the sugar acids derived from all of the aldoses and disaccharides that may be present in the corn syrup.

Corn syrups which are useful in the above process include Enzose™ Hydrol EO84 and EO81, Cerelose® Liquid Dextrose 2606, Royal® Glucose Liquid 2626 and Invertose® High Fructose Corn Syrup 2643 offered by Corn Products, Englewood Cliffs, N.J., 07632. Enzose™ hydrol EO84, which is a dextrose-rich liquor (corn molasses), has the following analysis:

Solids (%)—75.3
Dextrose Equivalent (min.)—72.0
Color—Clear dark
Ash (% sulfated, max.)—2.5

CARBOHYDRATE COMPOSITION

Dextrose—60.0
Disaccharides—20.0
Trisaccharides—4.0
Higher saccharides—16.0

Naphthaleneformaldehyde sulfonic acid is also known as the naphthalenesulfonic acid-formaldehyde condensates, formalin condensates of beta-naphthalenesulfonic acid, condensation products of naphthalenesulfonic acid with formaldehyde. Naphthaleneformaldehyde sulfonic acid may be prepared by reacting a mixture of naphthalene, formaldehyde and sulfuric acid. It may be prepared by the processes described in U.S. Pat. No. 2,141,569—Tucker et al, issued Dec. 27, 1938; U.S. Pat. No. 3,193,575—Nebel et al, issued July 6, 1965 and U.S. Pat. No. 3,277,162—Johnson, issued Oct. 4, 1966.

Naphthaleneformaldehyde sulfonic acid is a mixture of condensation products of naphthalenesulfonic acid and formaldehyde. It can be chromatographed by size exclusion chromatography through a column containing pore sizes which selectively separate molecular volumes according to size. The solvent chosen for the acid in chromatography should minimize solute-packing interaction and solute-solute interaction. The chromatogram gives a true molecular volume profile when the eluents are displayed on a detector-strip chart recorder display. For example, if the chromatrogram for a sample of the sulfonic acid is the same as that for the sodium naphthaleneformaldehyde sulfonate in U.S. Pat. No. 3,954,491—Adrian et al, issued May 4, 1976, the two anionic materials are identical. That is, the anionic materials from the acid have the same profile as the anionic materials from the sodium naphthaleneformaldehyde sulfonate having lowest elution volumes of from above 61 to about 70% of the total elution volume and equivalent elution volumes of from about 61 to about 70% of the total elution volume. The teachings in U.S. Pat. No. 3,954,491 relating to chromatography are incorporated by reference herein. This chromatographic method was described by Dr. Harold Edelstein in a paper entitled, "Aqueous Gel Permeation Chromatograph of Some Naphthalene Sulfonic Acid Formaldehyde Condensates" presented at the Mini Symposium of the North Jersey Chromatograph Group Subsection of the A.C.S. on Mar. 6, 1978 at Hoffman La Roche Auditorium, Clifton, N.J.

Sodium glucoheptonate is commercially available as a sodium glucoheptonate solution containing 50 to 70% solids. Attempts to concentrate a glucoheptonate solution to solid sodium glucoheptonate produces a tacky substance which is difficult to handle and use. Further, the ammoniacal odor of the sodium glucoheptonate solution is objectionable to personnel handling the solution on an industrial scale. The ammoniacal odor is particularly pronounced whenever the solution is added to an aqueous medium having a pH above 9.

The improved glucoheptonate compositions of the present invention are prepared by reacting an aqueous solution of a water soluble glucoheptonate salt such as sodium glucoheptonate after preparation with the free acid form of a naphthalenesulfonic acid-formaldehyde condensation product to produce an aqueous composition which does not have an ammoniacal odor even when added to aqueous media having a pH above 9. Equal parts by weight of the water soluble salt of glucoheptonate and free acid form of naphthalenesulfonic acid-formaldehyde condensation product may be reacted to obtain the improved composition. Likewise, the improved composition may be prepared by adding from about 2 to about 50% by weight of naphthalenesulfonic acid-formaldehyde condensation product to a 50% by weight of the water soluble glucoheptonate salt solution. Further, the improved glucoheptonate composition may be dried to obtain a solid brittle powder capable of being ground to a fine flowable powder. If desired, a carrier may be incorporated in the composition before or after drying. Water soluble glucoheptonate salts such as sodium, potassium, lithium, calcium, magnesium or zinc glucoheptonate may be used in these compositions with sodium glucoheptonate being preferred.

The improved aqueous glucoheptonate composition or flowable powder glucoheptonate composition may be added to a cement or concrete mix at any convenient point during its preparation or use. For example, the dried flowable powder composition may be added to portland cement clinker prior to grinding and thoroughly mixed with the cement during grinding. The dried, powdered composition may also be blended with the ground cement. Either the powdered glucoheptonate composition or liquid glucoheptonate composition may be added to the water in which the cement, sand and/or gravel are mixed. The cement may be premixed with water and then either the dried or liquid composition added. In general, either glucoheptonate composition may be added to the cement, mortar or concrete mix at any stage prior to final setting. Cement, mortar or concrete mixes include concretes, mortars, neat paste compositions, oil well cement slurries, grouting compositions and the like.

The cements used in the preparation of the concrete mixes include Type I, II and III cements. The properties of the cements are well known and are described in the Portland Cement Association Engineering Bulletin entitled, "Design and Control of Concrete Mixtures", Eleventh Edition, July 1968, and "KirkOthmer Encyclopedia of Chemical Technology," Second Edition (Interscience Publishers, N.Y., N.Y. 1967), Volume 4, pages 690-692. The teaching as to the properties of these cements are disclosed in these publications and are incorporated by reference herein.

These cements may be used to prepare concrete mixes containing 100 parts by weight of cement, from about 140 to about 260 parts by weight of sand, from about 100 to about 200 parts by weight of gravel, from about 35 to about 60 parts by weight of water and an effective amount of glucoheptonate composition sufficient to prolong the time of hydration of cement particles in concrete with the preferred concrete mixes containing 100 parts by weight of cement, from about 160 to about 230 parts by weight of sand, from about 140 to about 180 parts by weight of gravel, from about 38 to about 50 parts by weight of water and an effective amount of glucoheptonate composition sufficient to prolong the time of hydration of cement particles in concrete mixes. The concentration of glucoheptonate composition in the concrete mixes may vary from about 0.05 to about 3%, preferably from about 0.3 to about 1% (by weight of cement) to prolong the time of hydration of cement particles. After preparation, these concrete mixes are then allowed to harden to obtain hardened concretes.

In the drilling, completion and servicing of water, oil and gas wells, cement slurries are used to seal various portions of the well bore to anchor the well casing or for other purposes. the cement slurry may be pumped into the well bore under pressure and also subjected within the well bore to the hydrostatic pressure produced by a column of cement slurry which may be several hundred or thousand feet in height. Further, the slurry may be subjected to elevated temperatures within the borehole. These glucoheptonate compositions may be added to the cement slurry to prolong the time of hydration of cement particles in the slurry to permit proper placement of the cement slurry in the borehole.

Concentration of glucoheptonate composition in cement slurries may vary from about 0.05 to about 3%, preferably from about 0.1 to about 1% based on weight of cement to prolong the time of hydration of cement particles in the slurry. The glucoheptonate compositions of this invention may be added to the slurry or admixed in dry form with the cement before it is slurried.

Personnel using aqueous mixtures of cement or concrete containing water soluble glucoheptonate salts where residual byproduct ammonium ions were present objected to the strong ammonia odor produced by the alkaline mixture. However, they have not detected an ammonia odor when any glucoheptonate composition of this invention is added to an aqueous mixture of cement or concrete.

For a fuller understanding of the nature and advantages of this invention, reference may be made to the following examples. These examples are given merely to illustrate the invention and are not to be construed in a limiting sense. All quantities, proportions and percentages are by weight and all references to temperature are °C. unless otherwise indicated.

EXAMPLE I

This example demonstrates preparation of sodium glucoheptonate neutralized with a condensation product of naphthalenesulfonic acid and formaldehyde.

Mixed 880.3 g of corn syrup (Enzose TM Hydrol EO84) with 700.0 g of water in a reactor and added with agitation 164.9 g of powdered sodium cyanide. The reaction mixture was heated to 80° C. with agitation under vacuum. A scrubber containing 40 g of concentrated hydrochloric acid in 200 ml of water was placed in the vacuum line between the reactor and the vacuum pump. The reaction mixture was heated with agitation under vacuum at 80° C. for approximaely 3 hours (until a stable minimum pH of 10.0 was achieved). The mixture was then cooled to room temperature to obtain 1540.5 g of sodium glucoheptonate solution containing 50-55% solids and having a pH of 10.0.

Then 183.1 g of the condensation product of naphthalenesulfonic acid and formaldehyde was added to neutralize the sodium glucoheptonate solution to a pH of 7.0. Anionic materials in the condensation product of naphthalenesulfonic acid and formaldehyde has the same profile as anionic materials from sodium naphthaleneformaldehyde sulfonate having lowest elution volumes of from about 61 to about 70% of the total elution volume and equivalent elution volumes of from about 61 to about 70% of the total elution volume. The neutralized composition was dried at 110° C. for 24 hours to obtain a brittle solid mass which was then ground to a fine flowable powder that passes through a 200 mesh screen.

EXAMPLE II

Two samples of 50% by weight of glucoheptonate were prepared. One sample was a (untreated) control and the other (treated) sample contained in addition 5% of naphthalenesulfonic acid-formaldehyde condensation product having an equivalent elution by size exclusion chromatography of from about 61 to about 70% of the total elution.

The vapor phase above each sample was tested with moistured pH indicator paper. The vapor phase above the control sample had a strong ammoniacal odor and had a pH of 10 while the vapor phase above the treated sample had no ammoniacal odor and had a pH of 7.

Both samples were dried at 110° C. for 24 hours. The control sample was a solid tacky mass while the other sample was a solid brittle mass which was ground to a fine powder that passed completely through a 200 mesh screen.

EXAMPLE III

A mixture of 270 g of 50% by weight of glucoheptonate and 30 g of naphthalenesulfonic acid-formaldehyde condensation product having an equivalent elution by size exclusion chromatography of from about 30 to about 32% of the total elution was prepared having a pH of 9.5. The mixture was dried at 115° C. in an oven overnight to obtain a dry solid composition which could be easily ground to a fine powder. The finished product had a pH of 7.0.

EXAMPLE IV

These tests determine the time of hydration for cement by measuring the maximum temperature generated by the hydration of a sample of cement mortar in an isoperibol type calorimeter. The isoperibol calorimeter used in determining the time of hydration of the cement mortar is also known as an isothermal shield calorimeter, where the outer shield is maintained at a constant temperature throughout the test while the temperature of the specimen and specimen container is changing.

The calorimeter vessel includes an electric heater, a temperature measuring device (thermocouple) and the specimen being tested. Heat exchange between the calorimeter vessel and the shield is minimized by evacuating the space between them, by minimizing the amount of conductive material in the space, and by coating the relevant surfaces with a material of high reflectivity. A Dewar flask was found to be satisfactory as a calorimeter vessel and shield for these tests.

The sample of mortar was placed in the calorimeter and the temperature probe inserted in the sample and the calorimeter sealed. The temperaturetime profile is recorded for 24 hours and the time of hydration is determined by the time required for sample to reach maximum temperature. Further details on the procedure used in these tests are given below.

A 100 g sample of cement mortar was prepared using 50 g sand, 33 g portland cement and 17 g water. To this standard mortar was added the specific additive to be evaluated. The hydration time was recorded from the time that water came in contact with the cement.

The standard mix with additive was prepared according to ASTM Designation: C192-69. The mix was placed in the sample container and inserted into the calorimeter. A temperature probe was inserted into the mix. The calorimeter was sealed and the temperature recorder started. After 24 hours in the calorimeter, the time at which the mortar reached maximum temperature was determined from the recorder chart. All sample data were compared to the standard control mix (no additive).

The following results were obtained using the additives shown below at 0.5% O.W.C. (on weight of cement) in the standard mixture. Sodium glucoheptonate solution used as additive in these tests was a 50% by solids solution having a pH of 10. The condensation product of naphthalenesulfonic acid and formaldehyde had an equivalent elution by size exclusion chromatography of from about 61 to about 70% of the total elution.

| ADDITIVE | AMOUNT ADDED (O.W.C.) | HYDRATION TIME (HR) |
| --- | --- | --- |
| Sodium glucoheptonate | 0.5% | 14.25 |
| Naphthalenesulfonic acid-formaldehyde condensate | 0.5% | 11.25 |
| 50% by weight Sodium glucoheptonate and 50% by weight Naphthalenesulfonic acid-formaldehyde condensate | 0.5% | 19.25 |

A synergistic effect in the heat of hydration was observed. Hydration was retarded an additional five hours by using equal parts by weight of sodium glucoheptonate and naphthalenesulfonic acid-formaldehyde condensate.

While the invention has been described with reference to certain specific embodiments thereof, it is understood that it is not to be so limited since alterations and changes may be made therein which are within the full intended scope of the appended claims.

What is claimed is:

1. A process for eliminating ammonia odor from water soluble salt of glucoheptonate having present residual ammonium ion when said salt is introduced into aqueous media having a pH above 9, comprising adding to an aqueous solution of said glucoheptonate before introducing said glucoheptonate into said aqueous media a free acid form of naphthalenesulfonic acid-formaldehyde condensation product in an amount sufficient to react with said ammonium ion.

2. The process of claim 1 wherein the water soluble salt of glucoheptonate after reaction with the free acid form of naphthalenesulfonic acid-formaldehyde condensation product is dried to obtain a flowable powder.

3. The process of claim 1 wherein equal parts by weight of the water soluble salt of glucoheptonate and free acid form of naphthalenesulfonic acid-formaldehyde condensation product are reacted.

4. The process of claim 1 wherein about 2 to about 50% by weight of the naphthalenesulfonic acid-formaldehyde condensation product is reacted by addition to about 50% by weight of aqueous solution of the water soluble salt of glucoheptonate.

5. The process of claim 1 wherein the water soluble salt of glucoheptonate is selected from the group consisting of sodium, potassium, lithium, calcium, magnesium and zinc salts.

6. The process of claim 1 wherein the glucoheptonate salt is sodium glucoheptonate.

* * * * *